US010703763B2

(12) United States Patent
Viscomi et al.

(10) Patent No.: US 10,703,763 B2
(45) Date of Patent: *Jul. 7, 2020

(54) POLYMORPHOUS FORMS OF RIFAXIMIN, PROCESSES FOR THEIR PRODUCTION AND USE THEREOF IN THE MEDICINAL PREPARATIONS

(71) Applicant: ALFASIGMA S.P.A., Milan (IT)

(72) Inventors: Giuseppe Claudio Viscomi, Sasso Marconi (IT); Manuela Campana, Bologna (IT); Donatella Confortini, Calderara (IT); Maria Barbanti, Bologna (IT); Dario Braga, Bologna (IT)

(73) Assignee: ALFASIGMA S.P.A., Bologna (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/291,900

(22) Filed: Mar. 4, 2019

(65) Prior Publication Data

US 2020/0002350 A1 Jan. 2, 2020

Related U.S. Application Data

(63) Continuation of application No. 15/811,536, filed on Nov. 13, 2017, now abandoned, which is a continuation of application No. 15/481,413, filed on Apr. 6, 2017, now abandoned, which is a continuation of application No. 14/994,079, filed on Jan. 12, 2016, now abandoned, which is a continuation of application No. 14/262,612, filed on Apr. 25, 2014, now Pat. No. 9,271,968, which is a continuation of application No. 13/950,642, filed on Jul. 25, 2013, now Pat. No. 8,741,904, which is a continuation of application No. 13/488,345, filed on Jun. 4, 2012, now Pat. No. 8,518,949, which is a continuation of application No. 11/658,702, filed as application No. PCT/EP2006/001755 on Feb. 27, 2006, now Pat. No. 8,193,196.

(30) Foreign Application Priority Data

Mar. 3, 2005 (EP) .................................... 05004695

(51) Int. Cl.
 C07D 498/22 (2006.01)
 A61K 31/395 (2006.01)
 A61P 31/04 (2006.01)
 C07D 491/22 (2006.01)
 A61K 31/437 (2006.01)
 A61K 9/00 (2006.01)

(52) U.S. Cl.
 CPC .......... C07D 491/22 (2013.01); A61K 9/0053 (2013.01); A61K 31/437 (2013.01); C07D 498/22 (2013.01); C07B 2200/13 (2013.01)

(58) Field of Classification Search
 CPC ...... A61K 31/395; A61P 31/04; C07D 498/22
 See application file for complete search history.

(56) References Cited

U.S. PATENT DOCUMENTS

| 4,341,785 | A  | 7/1982  | Marchi et al.    |
|-----------|----|---------|------------------|
| 4,557,866 | A  | 12/1985 | Cannata et al.   |
| 5,356,625 | A  | 10/1994 | Ying             |
| 5,840,332 | A  | 11/1998 | Lerner et al.    |
| 5,886,002 | A  | 3/1999  | Ferrari et al.   |
| 6,861,053 | B1 | 3/2005  | Lin et al.       |
| 7,045,620 | B2 | 5/2006  | Viscomi et al.   |
| 7,452,857 | B2 | 11/2008 | Lin et al.       |
| 7,605,240 | B2 | 10/2009 | Lin et al.       |
| 7,612,199 | B2 | 11/2009 | Viscomi et al.   |
| 7,709,634 | B2 | 5/2010  | Kothakonda et al.|
| 7,718,608 | B2 | 5/2010  | Lin et al.       |
| 7,902,206 | B2 | 3/2011  | Viscomi et al.   |
| 7,906,542 | B2 | 3/2011  | Viscomi et al.   |
| 7,915,275 | B2 | 3/2011  | Viscomi et al.   |
| 7,923,553 | B2 | 4/2011  | Viscomi et al.   |
| 7,928,115 | B2 | 4/2011  | Forbes et al.    |
| 7,935,799 | B2 | 5/2011  | Lin et al.       |
| 8,158,644 | B2 | 4/2012  | Viscomi et al.   |
| 8,158,781 | B2 | 4/2012  | Viscomi et al.   |
| 8,173,801 | B2 | 5/2012  | Viscomi et al.   |

(Continued)

FOREIGN PATENT DOCUMENTS

| CA | 1215976 A | 12/1986 |
|----|-----------|---------|
| CA | 1218650 A | 3/1987  |

(Continued)

OTHER PUBLICATIONS

Written decision of the Controller of Mar. 1, 2017 with reference to the Pre-Grant Opposition against Indian Application No. 1865DEL2005. 52 pages.
Consolidated list of references in the Opposition documents against Indian Application No. 1865DEL2005. May 9, 2019. 1 page.
Viscomi, "Crystal forms of rifaximin and their effect on pharmaceutical properties", CrystEngComm, 2008, 10, pp. 1074-1081.
European Pharmacopeia Ed. 7.1, p. 3459-3460, 2011.
Grounds for the decision of the Opposition Division about the opposition against EP 1 698 630, Mar. 6, 2017. 14 pages.
Minute of the Oral Proceedings of the opposition against EP 1 698 630, Mar. 6, 2017. 4 pages.
Consolidated List of References in the Opposition Proceedings against EP1698630. May 9, 2019. 4 pages.

(Continued)

Primary Examiner — Bruck Kifle
(74) Attorney, Agent, or Firm — Steinfl + Bruno, LLP

(57) ABSTRACT

Crystalline polymorphous forms of the rifaximin (INN) antibiotic named rifaximin δ and rifaximin ε useful in the production of medicinal preparations containing rifaximin for oral and topical use and obtained by means of a crystallization process carried out by hot-dissolving the raw rifaximin in ethyl alcohol and by causing the crystallization of the product by addition of water at a determinate temperature and for a determinate period of time, followed by a drying carried out under controlled conditions until reaching a settled water content in the end product, are the object of the invention.

9 Claims, 2 Drawing Sheets

(56) References Cited

U.S. PATENT DOCUMENTS

| | | |
|---|---|---|
| 8,183,196 B2 | 5/2012 | Roberts et al. |
| 8,193,196 B2 | 6/2012 | Viscomi et al. |
| 8,217,054 B2 | 7/2012 | Maffei et al. |
| 8,227,482 B1 | 7/2012 | Parent et al. |
| 8,309,569 B2 | 11/2012 | Forbes et al. |
| 8,318,763 B2 | 11/2012 | Viscomi et al. |
| 8,404,704 B2 | 3/2013 | Viscomi et al. |
| 8,486,956 B2 | 7/2013 | Gushurst et al. |
| 8,507,517 B2 | 8/2013 | Parent et al. |
| 8,513,275 B2 | 8/2013 | Wu et al. |
| 8,518,949 B2 | 8/2013 | Viscomi et al. |
| 8,568,782 B2 | 10/2013 | Viscomi et al. |
| 8,569,326 B2 | 10/2013 | Gushurst et al. |
| 8,633,234 B2 | 1/2014 | Rao et al. |
| 8,642,573 B2 | 2/2014 | Forbes et al. |
| 8,735,419 B2 | 5/2014 | Parent et al. |
| 8,741,904 B2 | 6/2014 | Viscomi et al. |
| 8,748,447 B2 | 6/2014 | Viscomi et al. |
| 8,748,449 B2 | 6/2014 | Maffei et al. |
| 8,765,778 B2 | 7/2014 | Viscomi et al. |
| 8,815,888 B2 | 8/2014 | Wu et al. |
| 8,829,017 B2 | 9/2014 | Forbes et al. |
| 8,835,452 B2 | 9/2014 | Viscomi et al. |
| 8,853,231 B2 | 10/2014 | Viscomi et al. |
| 8,877,770 B2 | 11/2014 | Vigano' et al. |
| 8,883,795 B2 | 11/2014 | Kothakonda et al. |
| 8,946,252 B2 | 2/2015 | Forbes et al. |
| 8,952,159 B2 | 2/2015 | Lavagna et al. |
| 8,969,398 B2 | 3/2015 | Forbes |
| 9,018,225 B1 | 4/2015 | Hotha |
| 9,034,892 B2 | 5/2015 | Gushurst et al. |
| 9,035,046 B2 | 5/2015 | Golden et al. |
| 9,133,217 B2 | 9/2015 | Parent et al. |
| 9,186,355 B2 | 11/2015 | Hotha |
| 9,271,968 B2 | 3/2016 | Viscomi et al. |
| 9,273,066 B2 | 3/2016 | Gushurst et al. |
| 9,359,374 B2 | 6/2016 | Blazecka et al. |
| 9,364,467 B2 | 6/2016 | Golden et al. |
| 9,421,195 B2 | 8/2016 | Forbes et al. |
| 9,452,157 B2 | 9/2016 | Viscomi et al. |
| 9,498,442 B2 | 11/2016 | Viscomi et al. |
| 9,629,828 B2 | 4/2017 | Forbes et al. |
| 9,708,343 B2 | 7/2017 | Vigano' et al. |
| 9,725,466 B2 | 8/2017 | Golden et al. |
| 9,938,298 B2 | 4/2018 | Viscomi et al. |
| 9,988,398 B2 | 6/2018 | Sinigh |
| 2002/0107200 A1 | 8/2002 | Chang et al. |
| 2003/0059471 A1 | 3/2003 | Compton et al. |
| 2003/0157174 A1 | 8/2003 | Tsukuda et al. |
| 2004/0234601 A1 | 11/2004 | Legrand et al. |
| 2005/0196418 A1 | 9/2005 | Yu et al. |
| 2008/0262024 A1 | 10/2008 | Viscomi et al. |
| 2009/0028940 A1 | 1/2009 | Jahagirdar |
| 2011/0086871 A1 | 4/2011 | Viscomi et al. |
| 2012/0035202 A1 | 2/2012 | Viscomi et al. |
| 2012/0203000 A1 | 8/2012 | Viscomi et al. |
| 2012/0214989 A1 | 8/2012 | Viscomi et al. |
| 2012/0245192 A1 | 9/2012 | Viscomi et al. |
| 2012/0258166 A1 | 10/2012 | Viscomi et al. |
| 2013/0028971 A1 | 1/2013 | Viscomi et al. |
| 2014/0308350 A1 | 10/2014 | Viscomi et al. |
| 2015/0080421 A1 | 3/2015 | Viscomi et al. |
| 2015/0175627 A1 | 6/2015 | Viscomi et al. |
| 2015/0182508 A1 | 7/2015 | Viscomi et al. |
| 2017/0071916 A1 | 3/2017 | Viscomi et al. |
| 2017/0210757 A1 | 7/2017 | Viscomi et al. |
| 2018/0065987 A1 | 3/2018 | Viscomi et al. |
| 2018/0065988 A1 | 3/2018 | Viscomi et al. |
| 2018/0354971 A1 | 12/2018 | Viscomi et al. |

FOREIGN PATENT DOCUMENTS

| | | |
|---|---|---|
| EP | 0161534 B1 | 9/1989 |
| EP | 0547294 A1 | 6/1993 |
| EP | 0616808 A1 | 9/1994 |
| EP | 0547294 B1 | 11/1995 |
| EP | 0616808 B1 | 9/1996 |
| EP | 0935417 B1 | 8/1999 |
| EP | 0858804 B1 | 6/2002 |
| EP | 1557421 A1 | 7/2005 |
| EP | 1676847 A1 | 7/2006 |
| EP | 1 698 630 A1 | 9/2006 |
| EP | 1557421 B1 | 5/2007 |
| EP | 1 874 273 | 1/2008 |
| EP | 1676847 B1 | 1/2009 |
| EP | 1676848 B1 | 1/2009 |
| EP | 2011486 A1 | 1/2009 |
| EP | 2208730 A1 | 7/2010 |
| EP | 2210893 A1 | 7/2010 |
| EP | 2420226 A1 | 2/2012 |
| EP | 1698630 B1 | 9/2014 |
| EP | 2 927 235 A1 | 10/2015 |
| EP | 2927235 A1 | 10/2015 |
| EP | 2927235 B1 | 2/2017 |
| EP | 3126367 A1 | 2/2017 |
| EP | 2059232 B1 | 4/2017 |
| EP | 2618819 B1 | 11/2017 |
| EP | 3 294 270 B1 | 9/2018 |
| GB | 1317830 A | 5/1973 |
| GB | 2079270 A | 1/1982 |
| IT | BO 2005 A 000123 A | 9/2006 |
| IT | MI2005A000345 A | 9/2006 |
| IT | MI2006A001692 A | 3/2008 |
| JP | 2013184902 A | 9/2013 |
| NZ | 531622 A | 10/2004 |
| WO | 2005/044823 A2 | 5/2005 |
| WO | 2006/008512 A2 | 1/2006 |
| WO | 2006/094662 A1 | 9/2006 |
| WO | 2006/094737 A2 | 9/2006 |
| WO | 2006094143 A2 | 9/2006 |
| WO | 2006094144 A2 | 9/2006 |
| WO | 2006094181 A2 | 9/2006 |
| WO | 2008/029208 A1 | 3/2008 |
| WO | 2008/155728 A1 | 12/2008 |
| WO | 2009/008005 A1 | 1/2009 |
| WO | 2009/008006 A2 | 1/2009 |
| WO | 2009/047801 A1 | 4/2009 |
| WO | 2009/108730 A2 | 9/2009 |
| WO | 2010044093 A1 | 4/2010 |
| WO | 2010/067072 A1 | 6/2010 |
| WO | 2011/051971 A2 | 5/2011 |
| WO | 2011/061748 A1 | 5/2011 |
| WO | 2011050397 A1 | 5/2011 |
| WO | 2011061516 A2 | 5/2011 |
| WO | 2011061519 A2 | 5/2011 |
| WO | 2011/080691 A1 | 7/2011 |
| WO | 2011088688 A1 | 7/2011 |
| WO | 2011/103120 A1 | 8/2011 |
| WO | 2011/110930 A2 | 9/2011 |
| WO | 2011/153444 A1 | 12/2011 |
| WO | 2011/156897 A2 | 12/2011 |
| WO | 2012/009387 A1 | 1/2012 |
| WO | 2012/009388 A1 | 1/2012 |
| WO | 2012/038898 A1 | 3/2012 |
| WO | 2012035283 A1 | 3/2012 |
| WO | 2012/060675 A1 | 5/2012 |
| WO | 2012076832 A1 | 6/2012 |
| WO | 2012/109605 A2 | 8/2012 |
| WO | 2012/150561 A1 | 11/2012 |
| WO | 2012/155981 A1 | 11/2012 |
| WO | 2012/156533 A1 | 11/2012 |
| WO | 2012/156951 A1 | 11/2012 |
| WO | 2008/035109 A1 | 3/2013 |
| WO | 2014091432 A1 | 6/2014 |
| WO | 2014/186675 A1 | 11/2014 |
| WO | 2015/014984 A1 | 2/2015 |
| WO | 2015/150171 A1 | 10/2015 |
| WO | 2015/159275 A2 | 10/2015 |
| WO | 2015/173697 A1 | 11/2015 |
| WO | 2016/063289 A2 | 4/2016 |
| WO | 2017/021975 A1 | 2/2017 |
| WO | 2017/162725 A1 | 9/2017 |
| WO | 2017/162726 A1 | 9/2017 |
| WO | 2018158646 A1 | 9/2018 |

(56) References Cited

FOREIGN PATENT DOCUMENTS

| WO | 2018178777 A1 | 10/2018 |
|---|---|---|
| WO | 2018197538 A1 | 11/2018 |
| WO | 2019/003076 A1 | 1/2019 |

OTHER PUBLICATIONS http://www.salix.com/products_xifaxan.asp printout, Mar. 2017, 2 pages.
"Intrinsic Dissolution" from Monograph 1087 of U.S. Pharmacopoeia, 27. pp. 2512-2513. Apr. 2009.
Jiang, ZD et al. "In vitro activity and fecal concentration of rifaximin after oral administration", Antimicro Agent Chemother, 2000; 44: pp. 2205-2206.
Hoover, WW et al. "Antimicrobial activity and spectrum of Rifaximin, a new topical Rifamycin derivative", Diag Microbiol Infect Dis, 1993; 16: pp. 111-118.
The Guideline for Investigation of Bioequivalence, (CPMP/EWP/QEP/1401/98 Rev. 1/ Corr, Jan. 20, 2010), 27 pages.
Rossi et al., "NMR Studies of a New Class of Rifaximin-derived Molecules Rifaximin OR (Open Ring)" J. Chem. Research (S), 1996, 268-269.
Summary of Product Characteristics of Normix® (rifaximin) Apr. 23, 1985, (Original Italian + English translation) 12 pages.
European Patent No. 1557421, Opposition, Procedure according to Examples 7 and 9 as described in patent EP0161534. Nov. 21, 1985. 14 pages.
Sucker H. et al., "Pharmazeutische Technologie", Georg Thieme Verlag, 1991, pp. 145 to 149 and 244 to 247. (German + English translation).
Documents TM31.1-TM31.27 cited in the Nullity actions against EP 1 557 421 (DE 60 2004 006 367), Apr. 4, 2016. 87 pages (Italian Original + English translation).
Appeal brief concerning the nullity action of German part No. DE 60 2004 006 367 T2 of European Patent No. EP 1 557 421 B1. Dec. 15, 2016. 6 pages (German Original + English Translation).
Appeal substantiation filed by the Plaintiff concerning the nullity action of German part No. DE 60 2004 006 367 T2 of European Patent No. EP 1 557 421 B1. Mar. 14, 2017. 115 pages (German Original + English Translation).
Response to the appeal substantiation filed by the Defendant concerning the nullity action of German part No. DE 60 2004 006 367 T2 of European Patent No. EP 1 557 421 B1. Jul. 13, 2017. 89 pages (German Original + English Translation).
Notification of oral proceedings concerning the nullity action of German part No. DE 60 2004 006 367 T2 of European Patent No. EP 1 557 421 B1. Jan. 18, 2018. 5 pages (German Original + English Translation).
Consolidated List of References in the Nullity actions against EP 1 557 421 (DE 60 2004 006 367). Mar. 22, 2019. 7 pages.
Schwabe et al, Arzneiverordnungs-report 2016, Springer, Aug. 27, 2016, 5 pages (German Original + English Translation of Relevant Parts).
Schwabe et al, Arzneiverordnungs-report 2015, Springer, Aug. 18, 2015, 4 pages (German Original + English Translation of Relevant Parts).
Notice of appeal concerning the Opposition against European Patent N. 1 698 630. Apr. 18, 2017. 2 pages.
Appeal substantiation concerning the Opposition against European Patent N. 1 698 630. Jul. 6, 2017. 17 pages.
Opponent response to the appeal substantiation concerning the Opposition against European Patent N. 1 698 630. Dec. 12, 2017. 32 pages.
Appellant response to the appeal substantiation concerning the Opposition against European Patent N. 1 698 630. Jan. 23, 2018. 18 pages.
Consolidated List of References in the Opposition Proceedings against EP1698630. May 28, 2019.
Bernstein et al., "Concomitant Polymorphs", Angew. Chem. Int. Ed. 1999, 38, pp. 3440-3461.
Experimental Report, Preparation of Rifaximin Delta according to EP 1 698 630. Jul. 6, 2017. 2 pages.
Technical opinion by Professor Fabrizia Grepioni, Jun. 30, 2017, 5 pages.
Bacchi, et al., "Sampling rifamycin conformational variety by cruising through crystal forms: implications for polymorph screening and for biological models" Aug. 2008, New Journal of Chemistry, pp. 1725-1735.
Greenspan, "Humidity Fixed Points of Binary Saturated Aqueous solutions", Journal of Research of the National Bureau of Standards—A. Physics and Chemistry, vol. 81A, No. 1, Oct. 1976, pp. 89-96.
Grounds of opposition filed by Alfasigma S.p.A. against European Patent No. 2 927 235 B1. Nov. 8, 2017. 37 pgs.
Normix®: Certificate of Technical Characteristics (SmPC), Aug. 2009, 12 pages (Italian original + English translation).
Targaxan®: www.medicine.org.uk, Oct. 2016. 7 pages.
Australian Public Assessment report Xifaxan, May 17, 2012. 2 pages.
Viscomi et al., CrystEng Comm, 2008, 10, pp. 1074-1081.
Campbell S.N. et al., 2002, J. Pharm. Biomed. Anal. 28, pp. 1149-1159.
Bobrovs R. et al., 2012, J. Pharm. Sciences 101, pp. 4608-4614.
Marck Gibson, IHSHealth Group, 2001, pp. 403-440; Pharmaceutical Preformulation and Formulation.
Braga D. et al., Cryst Eng Comm, 2012, 14, pp. 6404-6411.
L.S. Zevin "Quantitative X-Ray Diffractometry", Ed. By I. Mureinik, 1995, pp. 5-7 Springer-Verlag, New York.
Jenkins and Snyder, "Introduction to X-ray Powder Diffractometry", Wiley & Sons Inc., Jun. 27, 1996, pp. 355-361.
Shankland, "Analytical Techniques in the Pharmaceutical Sciences", 2016, pp. 293-305.
Kidd, W. et al., Powder Diffraction, 8(3), Sep. 1993, pp. 180-187.
Declaration by Prof. Fabrizia Grepioni, Nov. 8, 2017, 8 pages.
Curriculum Vitae of Prof. Fabrizia Grepioni, Oct. 30, 2017, 2 pages.
Comparison of Figure 2 of WO 2009/108730 and Figure 2 of EP 2 927 235, Nov. 8, 2017, 1 page.
Table corresponding to Annex 2 filed by Patentee, with alignment of peaks. Dec. 13, 2018. 16 pages.
Appeal against decision of the Federal Patent Court on DE 60 2004 006 367 T2—Submission by Appellant (German original + English translation), Jun. 26, 2018. 63 pages.
Appeal against decision of the Federal Patent Court on DE 60 2004 006 367 T2—Minutes of the oral proceedings of Aug. 7, 2018. 20 pages. (German original + English translation).
Appeal against decision of the Federal Patent Court DE 60 2004 006 367 T2—Decision of the Federal Court of Justice. Dec. 11, 2018. 39 pages. (German original + English translation).
Appellee's test report D30 of the opposition appeal proceedings EP 1 698 630 filed with appeal substantiation of Jul. 6, 2017. 2 pages.
Appellee's appeal substantiation of Jul. 6, 2017 of EP 1 698 630. 17 pages.
European Patent No. 2927235, Opposition, Response to Notice of opposition Apr. 16, 2018. 44 pages.
European Patent No. 2927235, Opposition, Summons to attend Oral proceedings, Jul. 26, 2018. 13 pages.
European Patent No. 2927235, Opposition, Written submission by the Patentee, Dec. 12, 2018. 7 pages.
European Patent No. 2927235, Opposition, Written submission by the Opponent, Dec. 13, 2018. 22 pages.
European Patent No. 2927235, Opposition, Written submission by the Patentee, Jan. 14, 2019. 5 pages.
Characterization of crystalline and partially crystalline solids by X-ray powder diffraction (XRPD), U.S. Pharmacopeia 38th Ed. (2015), vol. 1, Reference No. 941, pp. 692 and 697.
Powder Diffraction: Theory and Practice. Edited by R. E. Dinnebier and S. J. L. Billinge. Cambridge: RSC Publishing, Mar. 2008. p. 125.
Alfa Wassermann Letter dated Sep. 10, 2008, 21 pages.
Dr. Sun Affidavit. Apr. 10, 2018, 20 pages.
Characterization of crystalline and partially crystalline solids by X-ray powder diffraction (XRPD), U.S. Pharmacopeia 35th Ed. (May 1, 2012), Reference No. 941, pp. 427-433.

(56) References Cited

OTHER PUBLICATIONS

Syloid® 244 FP Silica, Technical Data Sheet, Grace Davison Discovery Sciences, Apr. 2009, 2 pages.
Disodium Edetate, Handbook of Pharmaceutical Excipients 6th Ed.(Oct. 17, 2008), pp. 242-243.
Polyvinyl Alcohol, Handbook of Pharmaceutical Excipients 6th Ed.(Jan. 30, 2009), pp. 564-565.
ICH Harmonised Tripartite Guideline, Stability Testing of New Drug Substances and Products Q1A(R2), Current Step 4 version dated Feb. 6, 2003, 23 pages.
Curriculum vitae Dr. Viscomi. Dec. 13, 2018. 8 pages.
Notice of Allowance issued for U.S. Appl. No. 11/814,628, filed Jul. 24, 2007 on behalf of Giuseppe Claudio Viscomi, dated Aug. 29, 2013. 12 pages.
Notice of Allowance issued for U.S. Appl. No. 12/439,094, filed Feb. 26, 2009 on behalf of Giuseppe Claudio Viscomi, dated Feb. 17, 2012. 10 pages.
Notice of Allowance issued for U.S. Appl. No. 13/544,945, filed Jul. 9, 2012 on behalf of Giuseppe Claudio Viscomi, dated Feb. 10, 2014. 8 pages.
European Patent N. 1698630, Opposition, Notice of Appeal, Apr. 18, 2017. 2 pages.
European Patent N. 1698630, Opposition, Statement of Grounds for Appeal by Appellant. Jul. 6, 2017. 17 pages.
European Patent N. 1698630, Opposition, Response of the Opponent, Nov. 30, 2017. 27 pages.
European Patent N. 1698630, Opposition, Response of the Appellant, Jan. 23, 2018. 18 pages.
European Patent N. 2059232, Opposition, Minutes of the Oral Proceedings Apr. 4, 2019. 3 pages.
European Patent N. 2059232, Opposition, Decision revoking patent, Apr. 4, 2019. 18 pages.
European Patent N. 2059232, Appeal, Notice of Appeal, May 15, 2019. 2 pages.
European Patent N. 2059232, Appeal, Statement of Grounds for Appeal by Appellant. Aug. 1, 2019. 67 pages.
Declaration of G.C. Viscomi and Dr. Viscomi's CV dated May 6, 2019 filed in response to Non-Final Office Action dated Nov. 8, 2018 issued for U.S. Appl. No. 15/130,324, 15 pages.
European Patent N. 2618819, Opposition, Summons to attend Oral Proceedings + Preliminary non-binding opinion of the Opposition Division, Jul. 2, 2019. 13 pages.
European Patent No. 2927235, Opposition, Cancellation of Oral Proceedings. Jan. 29, 2019. 1 page.
Consolidated list of References in Opposition to No. 2 927 235 B1 (Euticals). Dec. 18, 2018. 3 pages.
Characterization of crystalline and partially crystalline solids by X-ray powder diffraction (XRPD), U.S. Pharmacopeia 38th Ed. (2015), Reference No. 941, pp. 692 and 697, 2015, 3 pages.
European Patent No. 2927235, Opposition, New Summons to attend to Oral Proceedings Jan. 31, 2019, 16 pages.
European Patent No. 2927235, Opposition, Written submission by the Patentee, May 10, 2019. 32 pages.
European Patent No. 2927235—X-ray diffraction report on rifaximin samples, Universidad de Burgos. May 9, 2019. 14 pages.
European Patent No. 2927235—Curriculum vitae of the person who performed the X-ray diffraction study, Pilar Castroviejo Fernandez, May 9, 2019. 3 pages.
European Patent No. 2927235, Opposition, Written submission by the Opponent, Jun. 26, 2019. 5 pages.
European Patent No. 2927235—Declaration by Prof. Braga in response to Experimental Report from University of Burgos Jun. 18, 2019. 3 pages.
European Patent No. 2927235—Curriculum vitae Prof. Braga, Jun. 18, 2019, 1page.
European Patent No. 2927235, Opposition, Minute of Oral Proceedings. Aug. 8, 2019. 17 pages.
European Patent No. 2927235, Opposition, Decision revoking European Patent. Aug. 8, 2019. 22 pages.

European Patent No. 1557421, Opposition, Patentee response to Notice of Opposition, Sep. 10, 2008. 22 pages.
European Patent No. 1557421, Opposition, EPO Decision rejecting the opposition, Jul. 8, 2009. 14 pages.
European Patent No. 1557421, Opposition, Notice of Appeal, Sep. 18, 2009. 1 page.
European Patent No. 1557421, Opposition, Statement of Grounds for Appeal, Nov. 18, 2009. 18 pages.
European Patent No. 1557421, Opposition, Response of the Patentee, Jun. 2, 2010. 29 pages.
European Patent No. 1557421, Opposition, Summons to attend Oral proceedings. Jun. 28, 2012. 13 pages.
European Patent No. 1557421, Opposition, Withdrawal of the Appeal, Feb. 5, 2013. 1 page.
European Patent No. 1557421, Opposition, Experiment according to Examples 7 and 9 as described in patent EP0161534 performed by the Opponent. Apr. 23, 2009. 4 pages.
Agenzia Italiana del Farmaco: Certificate of GMP Compliance of a Manufacturer. Department of Health & Human Services, letter dated Nov. 16, 2007. 3 pages.
Bacchi A. et al. Polymorphism-structure relationships of rifamexil, an antibiotic rifamycin derivative, Molecular Pharmacology, vol. 47, pp. 611-623. 1995.
Giron D. Thermal analysis and calorimetric methods in the characterisation of polymorphs and solvates, Thermochimica Acta, vol. 248, pp. 1-59. 1995.
Laird T. Development and scale-up process for the manufacture of new pharmaceuticals, 1990, pp. 321-359.
Miller S. Polymorphism-Interplay of Science and Regulation. SSCI—Pharmaceutical Solids, 2005.
Beckmann W., Seeding the desired polymorph background possibilities limitations and case studies, Org. Proc. Res. Dev., 2000, vol. 4, pp. 372-383.
Gionchetti P. et al. Antibiotic combination therapy in patients with chronic, treatment-resistant pouchitis, Alimentary Pharmacology and Therapeutics, 1999, vol. 23, pp. 713-718.
Paik Y. H., et al. Comparison of rifaximin and lactulose for the treatment of hepatic encephalopathy: a prospective randomized study, Yonsei Medical Journal, 2005, vol. 46, No. 3, pp. 399-407.
Declaration of Dario Braga dated Sep. 1, 2009 in response to Office Action dated Aug. 3, 2009 issued for U.S. Appl. No. 12/478,638, filed Sep. 3, 2009 and Dr. Braga's CV, 11 pages.
European Patent No. 2927235, Opposition; Experimental report. Dec. 13, 2018, filed in response to the summons to attend Oral proceedings pursuant to Rule 115(1) dated Jul. 26, 2018 + Dr. Viscomi's CV, 23 pages.
Brittain /Morris: Polymorphism in Pharmaceutical Solids, Drug and the Pharmaceutical Science, vol. 95, Chapter 4, 125-181. 1999.
Consolidated list of References in Opposition to EP1698630 (Application No. 05004695.2-1452). Jan. 16, 2020. 4 pages.
Consolidated list of References in Opposition to EP2059232. Jan. 16, 2020. 5 pages.
Consolidated list of References in Opposition against EP2618819. Jan. 16, 2020. 2 pages.
Consolidated list of References in the Opposition against EP2927235 (Application No. 14162587.0-1110) Apr. 17, 2020. 3 pages.
Consolidated list of References in the Opposition proceedings against EP1557421. Apr. 17, 2020. 3 pages.
European Patent N. 2618819 B1, Opposition, Notice of opposition to a European Patent, Jul. 31, 2018. 5 pages.
European Patent N. 2618819 B1, Opposition, Grounds of Opposition, Jul. 31, 2018. 19 pages.
European Patent N. 2618819, Opposition, Reply of the Patentee, Dec. 21, 2018. 24 pages.
Consolidated List of References cited in the Opposition against EP 2618819 B1. Dec. 21, 2018. 1 page.
Prantera C. et al., Rifaximin-extended intestinal release induces remission in patients with moderately active Crohn's diseas, Gastroenterology, 2012, 142, 473-481.
Palma-Aguirre J.A. et al., Bioavailability of two oral suspension and two oral tablet formulations of acyclovir 400 mg: Two single-dose,

(56) References Cited

OTHER PUBLICATIONS open-label, randomized, two-period crossover comparisons in healthy Mexican adult subjects, Clinical therapeutics, 2007, 29.6: 1146-1152.
Bacchieri A. et al., Fundamentals of Clinical Rearch, Springer-Verlag Italia, Milano, 2004, pp. 318-319, 332-333.
International Conference on Harmonisation, ICH topic E9: Statistical principle for clinical trials. (Feb. 1998). 39 pages.
Alfasigma S.p.A., Clinical study report, RETIC/03/06, Apr. 29, 2010, 5 pages.
Alfasigma S.p.A., Clinical study report, GRACE01. Apr. 2006, 4 pages.
*Civil Action* vs. *Actavis Laboratories FL, Inc.*, Stipulated Consent Judgement and Injunction. Sep. 17, 2018. 4 pages.
*Civil Action* vs. *Actavis Laboratories FL, Inc.*, Report to the Patent and Trademark Office, dated Sep. 17, 2018. 6 pages.
Corazza G.R. et al., "Treatment of Small Intestine Bacterial Overgrowth with Rifaximin, a Non-absorbable Rifamycin", J. Int. Med. Res, 16, May 1988, pp. 312-316.
Husebye E., "Gastrointestinal motility disorders and bacterial overgrowth", J. Intern. Med , 237(4), Jan. 1995, pp. 419-427.
Peeters T.L. et al., "Effect of Motilin on Gastric Emptying in Patients With Diabetic Gastroparesis", Gastroenterology, 102(1), Jan. 1992, pp. 97-101.
Beseghi U. et al., "Comparison of two non-absorbable antibiotics for treatment of bacterial enteritis in children", Eur Rev Med Pharmacol Sci, 3-4, May 1998, pp. 131-136.
Lynn et al. "Irritable Bowel Syndrome", N. Engl. J. Med., vol. 329, No. 26, Dec. 1993, pp. 1940-1945.
Hardman et al., "Chapter 1 Pharmacokinetics", Goodman & Gillman's The Pharmacological Basis of Therapeutics, McGraw-Hill , 10° Ed., Jan. 2001, pp. 15-17.
Scarpignato C. et al., "Rifaximin, A Poorly Absorbed Antibiotic: Pharmacology and Clinical Use", edited by C. Scarpignato, Chemotherapy, vol. 51, Suppl. I, 2005, pp. 36-66.
Sama C. et al., "Clinical Effects of Rifaximin in Patients with Hepatic Encephalopathy Intolerant or Nonresponsive to Previous Lactulose Treatment: An Open-Label, Pilot Study", Sep. 2004, Curr. Ther. Res, 65(5), pp. 413-422.
Puxeddu A. et al., "Rifaximin in the treatment of chronic hepatic encephalopathy", Curr. Med. Res. Opin., 13(5), Jan. 1995, pp. 274-281.
Adachi J.A. et al., "Rifaximin: A Novel Nonabsorbed Rifamycin for Gastrointestinal Disorders", Clin. Infect. Diseases, 42, Jan. 2006, pp. 541-547.
Lichtenstein G.R. et al., "Rifaximin: Recent Advances in Gastroenterology and Hepatology", Jun. 2007, pp. 474-483, 3(6), Gastroenterology and Hepatology.
Paik Y.H. et al., "Comparison of Rifaximin and Lactulose for the Treatment of Hepatic Encephalopathy: A Prospective Randomized Study", 46(3), Yonsei Med. J., Jan. 2005, pp. 399-407.
Shen B. et al., "Oral Rifaximin as Maintenance Therapy for Antibiotic-Dependent Pouchitis", Amer. J. Gastroenterology, 101(9), Sep. 2006, S441-42, 1130.
Durand, et al. "Assessment of the prognosis of cirrhosis: Child—Pugh versus MELD", J. Hepatology, 42, Jan. 2005, S100-S107.
Sivapalasingam S., "Rifaximin: A useful drug for travelers' diarrhea". Taken from <http://www.clinicalcorrelations.org/?p=475>, Clinical Correlations, NYU Langone Online J. of Med. Sep. 2007, 2 pages.
Pimentel M. et al., "The Effect of a Nonabsorbed Oral Antibiotic (Rifaximin) on the Symptoms of the Irritable Bowel Syndrome", Ann. Intern, Med. 145(8), Oct. 2006, pp. 557-563.
"Study to Assess the Efficacy and Safety of Rifaximin Administered BID in the Treatment of Patients With Diarrhea-Associated Irritable Bowel Syndrome". Taken from <https://clinicaltrials.gov/ct2/show/study/NCT002694123>, US National Library of Medicine, Dec. 2005. 3 pages.

Nies A., Goodman & Gillman's The Pharmacological Basis of Therapeutics, Chapter 4 Principles of Therapeutics, 8th Ed., Pergamon Press, Jan. 1990, pp. 62-65 and 74-77 (8 pgs total).
Lipsky M.S. et al., "From Idea to Market: The Drug Approval Process", J. Am. Board Fam. Med., 14(5), Sep. 2001, pp. 362-367.
European Patent N. 2059232 B1, Opposition, Notice of Opposition. Feb. 7, 2018. 3 pages.
European Patent N. 2059232 B1, Opposition, Grounds of opposition filed by Zaklady Farmaceutyczne Polpharma S.A. (Opponent 1). Jan. 17, 2018. 19 pages.
European Patent N. 2059232 B1, Opposition, Grounds of opposition filed by Sandoz Gmbh (Opponent 2). Jan. 19, 2018. 23 pages.
European Patent N. 2059232 B1, Opposition, Grounds of opposition filed by Pentafarma ociedade Tecnico-Medicinal S.A. (Opponent 3), Jan. 19, 2018. 25 pages.
European Patent N. 2059232 B1, Opposition, Response of the Patentee, Jun. 1, 2018. 36 pages.
European Patent N. 2059232 B1, Opposition, Summons to attend Oral Proceedings, Jul. 12, 2018. 9 pages.
European Patent N. 2059232 B1, Opposition, Response to the Summons to attend oral proceedings by Patentee, Nov. 21, 2018. 14 pages.
European Patent N. 2059232 B1, Opposition, Response by Opponent 2, Nov. 23, 2018. 9 pages.
European Patent N. 2059232 B1, Opposition, Response Brief of the Patentee Jan. 8, 2019. 4 pages.
European Patent N. 2059232 B1, Opposition, Response of Opponent 2, Jan. 16, 2019. 4 pages.
Consolidated List of References cited in the Opposition against EP 2059232 B1. Nov. 21, 2018. 3 pages.
Summary of Product Characteristics of Normix® in the Czech Republic in 2003 (Czech original + English translation). 6 pages.
Rowe R. C., et al., Handbook of pharmaceutical excipients. London: Pharmaceutical press, 5th Ed., 2006., p. 217-221.
Rifaximin, printout from Wikipedia, Dec. 31, 2017. 4 pages.
Cellulose, printout from Wikipedia, Jan. 7, 2018. 8 pages.
Figures 1 and 5 of the opposed patent with indication of polymorph α peaks according to TM1 (D13). Jan. 18, 2018. 2 pages.
Figure 4 of the opposed patent with indication of polymorph beta peaks according to TM1 (D13). Jan. 18, 2018. 2 pages.
European Patent No. EP 2 059 232, Opposition, Experimental report process according to claim 13 of EP2059323B1. Jan. 11, 2018. 4 pages.
Excerpt from European Patent Bulletin Feb. 2008. Jan. 9, 2008. 1 page.
Excerpt from European Patent Register EP 1 874 273. Jan. 16, 2018. 2 pages.
Excerpt from the Italian Patent Register of BO 2005 A 000123 (Italian original + English translation). May 15, 2018. 2 pages.
Excerpt from the INPADOC patent family list of BO 2005 A 000123. Jan. 15, 2018. 1 page.
Ritschel, "Die Tablette", Editio Cantor Verlag, 2nd edition 2002, pp. 28, 584, (German Original + English Translation).
Request for correction of figures. Sep. 10, 2008. 4 pages.
ICH Harmonised Tripartite Guideline, Specifications: Test Procedures and Acceptance Criteria for New Drug Substances and New Drug p. 35 pages.Roducts: Chemical Substances, Q6A, Oct. 6, 1999. 35 pages.
Declaration by Prof. Grepioni, Dec. 12, 2011. 5 pages.
Declaration of UIBM of Apr. 27, 2018 (Italian original + English translation).2 pages.
Declaration of UIBM of May 9, 2018 (Italian original + English translation). 2 pages.
Request for correction of Table 1 of Italian Patent No. 1.375.471, Dec. 29, 2010. 10 pages. (Italian Original + English Translation).
Extract from the Register of UIBM concerning the Italian Patent Application No. B02005A000123. May 15, 2018. English+ Italian. 8 pages.
European Patent N. 2059232, Opposition, "Experimental report I". Nov. 21, 2018. 10 pages.
European Patent N. 2059232, Opposition, "Experimental report II". Nov. 21, 2018. 14 pages.
Curriculum Vitae Dr. Giuseppe Viscomi. Nov. 21, 2018. 8 pages.

(56) References Cited

OTHER PUBLICATIONS

European Patent N. 2059232, Opposition, Overlays of Figures of "Experimental report I". Jan. 16, 2019. 4 pages.
European Patent N. 2059232, Opposition, Overlays of Figures of "Experimental report II". Jan. 16, 2019. 1 page.
European Patent N. 2059232, Observation by Third Parties, Mar. 20, 2015. 5 pages.
Decision of the Board of Appeal No. G2/88, Dec. 11, 1989. 33 pages.
European Patent N. 2059232, Observation by Third Parties, Jan. 19, 2016. 2 pages.
European Patent N. 2059232, Observation by Third Parties, May 2, 2016. 2 pages.
Revised Xifaxan Label, May 21, 2004. 13 pages.
Zaxine, Technical Data Sheet (Spanish original + English translation). Sep. 2000. 10 pages.
Xifaxan Rifaximina Label Salix Pharmaceuticals Inc. Jan. 2018. 27 pages.
European Patent N. 2059232, Observation by Third Parties, Nov. 15, 2016. 1 page.
European Patent N. 2059232, Observation by Third Parties, Nov. 21, 2016. 2 pages.
European Patent N. 3294270, Opposition, Grounds of Opposition, Jun. 12, 2019. 22 pages.
Consolidated list of references in Opposition against European Patent N. EP 3294270, 1 page. Apr. 17, 2020.
Rifaximin, printout from Wikipedia (German + English version), Jun. 12, 2019, 9 pages.
Blandizzi et al. Impact of crystal polymorphism on the systemic bioavailability of rifaximin, an antibiotic acting locally in the gastrointestinal tract, in healthy volunteers, Drug Design, Development and Therapy 2015, 9: 1-11.
Khadka et al. Pharmaceutical particle technologies: An approach to improve drug solubility, dissolution and bioavailability. Asian Journal of Pharmaceutical Sciences, 2014; 9: 304-316.
European Patent N. 3294270; Experimental Report according to Example 3 of EP 3 294 270 B1. Jun. 7, 2019 + CV Viscomi. 11 pages.
W.A. Ritschel, A. Bauer-Brandl: "Die Tablette", Ed. Cantor Verlag, 2002, 260-261 (original German + English translation) 7 pages.
Pimentel M. Rifaximin Therapy for Patients with Irritable Bowel Syndrome without Constipation, N Engl J Med 2011; 364: 22-32.

POLYMORPHOUS FORMS OF RIFAXIMIN, PROCESSES FOR THEIR PRODUCTION AND USE THEREOF IN THE MEDICINAL PREPARATIONS

RELATED APPLICATIONS

The present application is a continuation under 35 U.S.C. § 120 of U.S. patent application Ser. No. 15/811,536 filed Nov. 13, 2017, which is a continuation of U.S. patent application Ser. No. 15/481,413 filed on Apr. 6, 2017, which is a continuation of U.S. patent application Ser. No. 14/994,079 filed on Jan. 12, 2016, which is a continuation of U.S. patent application Ser. No. 14/262,612 filed on Apr. 25, 2014, now U.S. Pat. No. 9,271,968 issued on Mar. 1, 2016, which is a continuation under 35 U.S.C. § 120 of U.S. patent application Ser. No. 13/950,642 filed Jul. 25, 2013, now U.S. Pat. No. 8,741,904, issued on Jun. 3, 2014, which is a continuation under 35 U.S.C. § 120 of U.S. patent application Ser. No. 13/488,345, filed Jun. 4, 2012, now U.S. Pat. No. 8,518,949, issued on Aug. 27, 2013, which is a continuation of U.S. patent application Ser. No. 11/658,702, filed Oct. 8, 2007, now U.S. Pat. No. 8,193,196, issued on Jun. 5, 2012, which in turn is filed under 35 U.S.C. § 371 as the U.S. national application of International Patent Application No. PCT/EP2006/001755, filed Feb. 27, 2006, which in turn claims priority to the European Patent Application No. EP 05004695.2, filed Mar. 3, 2005, the entire disclosure of all of which is hereby incorporated by reference herein, including the drawings.

BACKGROUND OF THE INVENTION

The rifaximin (INN; see The Merck Index, XIII Ed., 8304) is an antibiotic pertaining to the rifamycin class, exactly it is a pyrido-imidazo rifamycin described and claimed in the Italian Patent IT 1154655, while the European Patent EP 0161534 describes and claims a process for its production starting from the rifamycin O (The Merck Index, XIII Ed., 8301).

Both these patents describe the purification of the rifaximin in a generic way saying that the crystallization can be carried out in suitable solvents or solvent systems and summarily showing in some examples that the product coming from the reaction can be crystallized from the 7:3 mixture of ethyl alcohol/water and can be dried both under atmospheric pressure and under vacuum without saying in any way neither the experimental conditions of crystallization and drying, nor any distinctive crystallographic characteristic of the obtained product.

The presence of different polymorphs had not been just noticed and therefore the experimental conditions described in both patents had been developed with the goal to get a homogeneous product having a suitable purity from the chemical point of view, apart from the crystallographic aspects of the product itself.

It has now be found, unexpectedly, that some polymorphous forms exist whose formation, in addition to the solvent, depends on the conditions of time and temperature at which both the crystallization and the drying are carried out.

These orderly polymorphous forms will be, later on, conventionally identified as rifaximin δ (FIG. 1) and rifaximin ε (FIG. 2) on the basis of their respective specific diffractograms reported in the present application.

The polymorphous forms of the rifaximin have been characterized through the technique of the powder X-ray diffraction.

The identification and characterization of these polymorphous forms and, contemporarily, the definition of the experimental conditions for obtaining them is very important for a compound endowed with pharmacological activity which, like the rifaximin, is marketed as medicinal preparation, both for human and veterinary use. In fact it is known that the polymorphism of a compound that can be used as active principle contained in a medicinal preparation can influence the pharmaco-toxicologic properties of the drug. Different polymorphous forms of an active principle administered as drug under oral or topical form can modify many properties thereof like bioavailability, solubility, stability, color, compressibility, flowability and workability with consequent modification of the profiles of toxicological safety, clinical effectiveness and productive efficiency.

What above mentioned is confirmed with authority by the fact that the authorities that regulate the grant of the authorization for the admission of the drugs on the market require that the manufacturing methods of the active principles are standardized and controlled in such a way that they give homogeneous and sound results in terms of polymorphism of the production batches (CPMP/QWP/96, 2003—Note for Guidance on Chemistry of new Active Substance; CPMP/ICH/367/96—Note for guidance specifications: test procedures and acceptance criteria for new drug substances and new drug products: chemical substances; Date for coming into operation: May 2000).

The need of the above-mentioned standardization has further been strengthened just in the field of the rifamycin antibiotics from Henwood S. Q., de Villiers M. M., Liebenberg W. and Lotter A. P., Drug Development and Industrial Pharmacy, 26 (4), 403-408, (2000), who have ascertained that different production batches of the rifampicin (INN) made from different manufacturers differ among them because they show different polymorphous characteristics, and as a consequence they show different profiles of dissolution together with consequent alteration of the respective pharmacological properties.

By applying the processes of crystallization and drying generically disclosed in the previous patents IT 1154655 and EP 0161534 it has been found that under some experimental conditions the poorly crystalline form of the rifaximin is obtained while under other experimental conditions the other crystalline polymorphous forms of the rifaximin are obtained. Moreover it has been found that some parameters, absolutely not disclosed in the above-mentioned patents, like for instance the conditions of preservation and the relative humidity of the ambient, have the surprising effect to determine the form of the polymorph.

The polymorphous forms of the rifaximin object of the present patent application were never seen or hypothesized while thinking that a sole homogeneous product would always have been obtained whichever method would have been chosen within the range of the described conditions, irrespective of the conditions used for crystallizing, drying and preserving.

It has now been found that the formation of the δ and ε forms depends on the presence of water within the crystallization solvent, on the temperature at which the product is crystallized and on the amount of water present into the product at the end of the drying phase.

The form δ and the form ε of the rifaximin have then been synthesized and they are the object of the invention.

In particular the form δ is characterized by the residual content of water in the dried solid material in the range from 2.5% and 6% (w/w), more preferably from 3% and 4.5%, while the form ε is the result of a polymorphic transition under controlled temperature moving from the form δ.

These results have a remarkable importance as they determine the conditions of industrial manufacturing of some steps of working which could not be considered critical for the determination of the polymorphism of a product, like for instance the maintaining to a crystallized product a quantity of water in a stringent range of values, or the process of drying the final product, in which a form, namely form δ, has to be obtained prior to continuing the drying to obtain the form δ, or the conditions of preservation of the end product, or the characteristics of the container in which the product is preserved.

Rifaximin exerts its broad antibacterial activity in the gastrointestinal tract against localized gastrointestinal bacteria that cause infectious diarrhea including anaerobic strains. It has been reported that rifaximin is characterized by a negligible systemic absorption, due to its chemical and physical characteristics (Descombe J. J. et al. Pharmacokinetic study of rifaximin after oral administration in healthy volunteers. Int J Clin. Pharmacol. Res., 14 (2), 51-56, (1994))

Now we have found that it is possible on the basis of the two identified polymorphic forms of rifaximin to modulate its level of systemic adsorption, and this is part of the present invention, by administering distinct polymorphous forms of rifaximin, namely rifaximin δ and rifaximin ε. It is possible to have a difference in the adsorption of almost 100 folds in the range from 0.001 to 0.3 µg/ml in blood.

The evidenced difference in the bioavailability is important because it can differentiate the pharmacological and toxicological behavior of the two polymorphous of rifaximins δ and ε.

As a matter of fact, rifaximin ε is negligibly absorbed through the oral route while rifaximin δ shows a mild absorption.

Rifaximin ε is practically not absorbed, might act only through a topical action, including the case of the gastrointestinal tract, with the advantage of very low toxicity.

On the other way, rifaximin δ, which is mildly absorbed, can find an advantageous use against systemic microorganisms, able to hide themselves and to partially elude the action of the topic antibiotics.

In respect of possible adverse events coupled to the therapeutic use of rifaximin of particular relevance is the induction of bacterial resistance to the antibiotics. Generally speaking, it is always possible in the therapeutic practice with antibiotics to induce bacterial resistance to the same or to other antibiotic through selection of resistant strains.

In case of rifaximin, this aspect is particularly relevant, since rifaximin belongs to the rifamycin family, a member of which, the rifampicin, is largely used in tuberculosis therapy. The current short course treatment of tuberculosis is a combination therapy involving four active pharmaceutical ingredients: rifampicin, isoniazid, ethambutol and pyrazinamide and among them rifampicin plays a pivotal role. Therefore, any drug which jeopardized the efficacy of the therapy by selecting for resistance to rifampicin would be harmful. (Kremer L. et al. "Re-emergence of tuberculosis: strategies and treatment", Expert Opin. Investig. Drugs, 11 (2), 153-157, (2002)).

In principle, looking at the structural similarity between rifaximin and rifampicin, it might be possible by using rifaximin to select resistant strains of *M. tuberculosis* and to induce cross-resistance to rifampicin. In order to avoid this negative event it is crucial to have a control of quantity of rifaximin systemically absorbed.

Under this point of view, the difference found in the systemic absorption of the δ and ε forms of the rifaximin is significant, since also at sub-inhibitory concentration of rifaximin, such as in the range of from 0.1 to 1 µg/ml, selection of resistant mutants has been demonstrated to be possible (Marchese A. et al. In vitro activity of rifaximin, metronidazole and vancomycin against *Clostridium difficile* and the rate of selection of spontaneously resistant mutants against representative anaerobic and aerobic bacteria, including ammonia-producing species. Chemotherapy, 46(4), 253-266, (2000)).

According to what above said, the importance of the present invention, which has led to the knowledge of the existence of the above mentioned rifaximin polymorphous forms and to various industrial routes for manufacturing pure single forms having different pharmacological properties, is clearly strengthened.

The above-mentioned δ and ε forms can be advantageously used as pure and homogeneous products in the manufacture of medicinal preparations containing rifaximin.

As already said, the process for manufacturing rifaximin from rifamycin O disclosed and claimed in EP 0161534 is deficient from the point of view of the purification and identification of the product obtained; it shows some limits also from the synthetic point of view as regards, for instance, the very long reaction times, from 16 to 72 hours, very little suitable for an industrial use and moreover because it does not provide for the in situ reduction of the rifaximin oxidized that may be formed within the reaction mixture.

Therefore, a further object of the present invention is an improved process for the industrial manufacturing of the δ and ε forms of the rifaximin, herein claimed as products and usable as defined and homogeneous active principles in the manufacture of the medicinal preparations containing such active principle.

DESCRIPTION OF THE INVENTION

Figure 1:
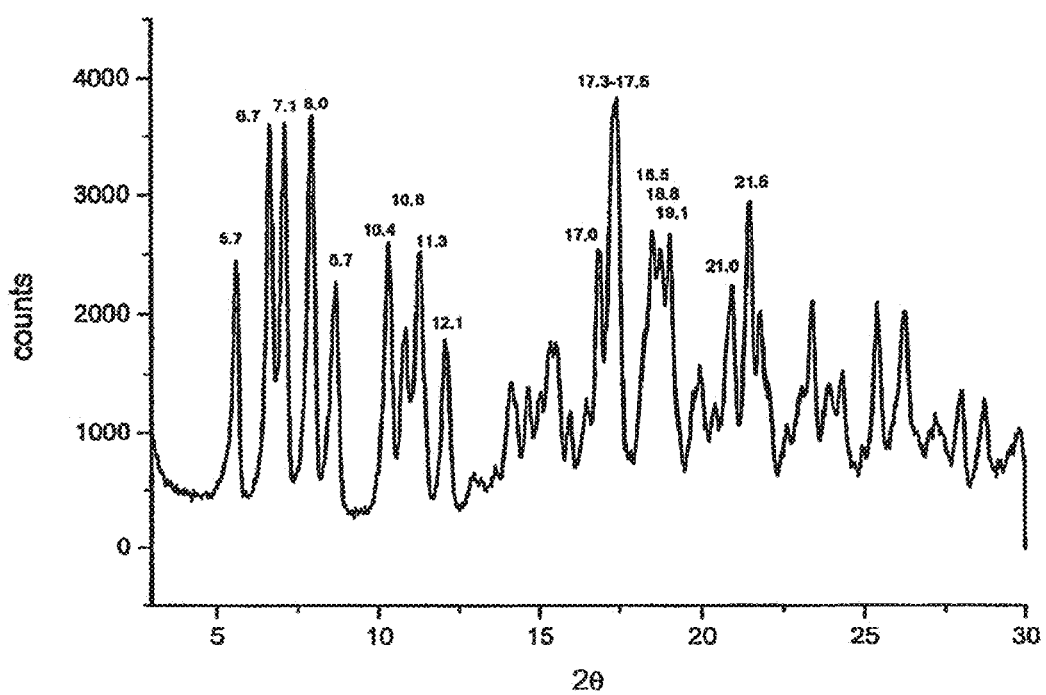
FIG. 1 is a powder X-ray diffractogram of rifaximin δ.

As already said, the form δ and the form ε of the antibiotic known as rifaximin (INN), processes for their production and the use thereof in the manufacture of medicinal preparations for oral or topical route, are object of the present invention.

A process object of the present invention comprises reacting one molar equivalent of rifamycin O with an excess of 2-amino-4-methylpyridine, preferably from 2.0 to 3.5 molar equivalents, in a solvent mixture made of water and ethyl alcohol in volumetric ratios between 1:1 and 2:1, for a period of time between 2 and 8 hours at a temperature between 40° C. and 60° C.

At the end of the reaction the reaction mass is cooled to room temperature and is added with a solution of ascorbic acid in a mixture of water, ethyl alcohol and aqueous concentrated hydrochloric acid, under strong stirring, in order to reduce the small amount of oxidized rifaximin that forms during the reaction and finally the pH is brought to about 2.0 by means of a further addition of concentrated aqueous solution of hydrochloric acid, in order to better remove the excess of 2-amino-4-methylpyridine used in the reaction. The suspension is filtered and the obtained solid is washed with the same solvent mixture water/ethyl alcohol used in the reaction. Such semi finished product is called "raw rifaximin".

The raw rifaximin can be directly submitted to the subsequent step of purification. Alternately, in case long times of preservation of the semi finished product are expected, the raw rifaximin can be dried under vacuum at a temperature lower than 65° C. for a period of time between 6 and 24 hours, such semi finished product is called "dried raw rifaximin".

The so obtained raw rifaximin and/or dried raw rifaximin are purified by dissolving them in ethyl alcohol at a temperature between 45° C. and 65° C. and by crystallizing them by addition of water, preferably in weight amounts between 15% and 70% in respect of the amount by weight of the ethyl alcohol used for the dissolution, and by keeping the obtained suspension at a temperature between 50° C. and 0° C. under stirring during a period of time between 4 and 36 hours.

The suspension is filtered and the obtained solid is washed with water and dried under vacuum or under normal pressure, with or without a drying agent, at a temperature between the room temperature and 105° C. for a period of time between 2 and 72 hours.

The achievement of the δ and ε forms depends on the conditions chosen for the crystallization. In particular, the composition of the solvent mixture from which the crystallization is carried out, the temperature at which the reaction mixture is kept after the crystallization and the period of time at which that temperature is kept, have proven to be critical.

More precisely, the δ and ε rifaximins are obtained when the temperature is first brought to a value between 28° C. and 32° C. in order to cause the beginning of the crystallization, then the suspension is brought to a temperature between 40° C. and 50° C. and kept at this value for a period of time between 6 and 24 hours, then the suspension is quickly cooled to 0° C., in a period of time between 15 minutes and one hour, is filtered, the solid is washed with water and then is dried.

The step of drying has an important part in obtaining the δ and ε polymorphous forms of the rifaximin and has to be checked by means of a suitable method fit for the water dosage, like for instance the Karl Fisher method, in order to check the amount of remaining water present in the product under drying.

The obtaining of the rifaximin δ during the drying in fact depends on the end remaining amount of water which should be comprised from 2.5% (w/w) and 6% (w/w), more preferably between-3% and 4.5%, and not from the experimental conditions of pressure and temperature at which this critical limit of water percent is achieved.

In order to obtain the poorly adsorbed ε form it has to start from the δ form and it has to be continued the drying under vacuum or at atmospheric pressure, at room temperature or at high temperatures, in the presence or in the absence of drying agents, provided that the drying is prolonged for the time necessary so that the conversion in form E is achieved.

Both the forms δ and ε of the rifaximin are hygroscopic, they absorb water in a reversible way during the time in the presence of suitable conditions of pressure and humidity in the ambient and are susceptible of transformation to other forms.

The transitions from one form to another result to be very important in the ambit of the invention, because they can be an alternative manufacturing method for obtaining the form desired for the production of the medicinal preparations. Therefore, the process that allows to turn the rifaximin δ into rifaximin ε in a valid industrial manner is important part of the invention.

The process concerning the transformation of the rifaximin δ into rifaximin ε comprises drying the rifaximin δ under vacuum or at atmospheric pressure, at room temperature or at high temperatures, in the presence or in the absence of drying agents, and keeping it for a period of time until the conversion is obtained, usually between 6 and 36 hours.

From what above said, it results that during the phase of preservation of the product a particular care has to be taken so that the ambient conditions do not change the water content of the product, by preserving the product in ambient having controlled humidity or in closed containers that do not allow in a significant way the exchange of water with the exterior ambient.

Figure 2:
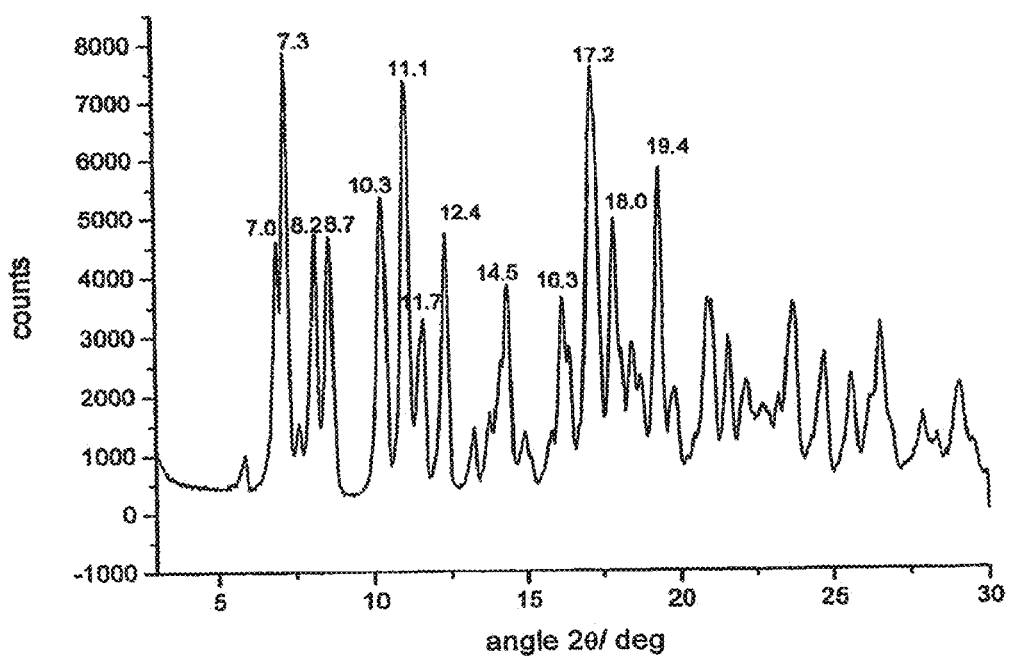
FIG. 2 is a powder X-ray diffractogram of rifaximin ε.

The polymorph called rifaximin δ is characterized from a content of water in the range between 2.5% and 6%, preferably between 3.0% and 4.5% and from a powder X-ray diffractogram (reported in FIG. 1) which shows peaks at the values of the diffraction angles 2θ of 5.70°±0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2, 21.5°±0.2. The polymorph called rifaximin ε is characterized from a powder X-ray diffractogram (reported in FIG. 2) which shows peaks at the values of the diffraction angles 2θ of 7.0°±0.2, 7.3°±0.2, 8.2°±0.2, 8.7°±0.2, 10.3°±0.2, 11.10°±0.2, 11.7°±0.2, 12.4°±0.2, 14.5°±0.2, 16.3°±0.2, 17.2±0.2, 18.0°±0.2, 19.4±±0.2.

The diffractograms have been carried out by means of the Philips X'Pert instrument endowed with Bragg-Brentano geometry and under the following working conditions:

X-ray tube: Copper
Radiation used: K ($\alpha$1), K ($\alpha$2)
Tension and current of the generator: KV 40, mA 40
Monochromator: Graphite
Step size: 0.02
Time per step: 1.25 seconds
Starting and final angular 2θ value: 3.0°/30.0°

The evaluation of the content of water present in the analysed samples has always been carried out by means of the Karl Fisher method.

Rifaximin δ and rifaximin ε differ each from other also because they show significant differences as regards bioavailability.

A bioavailability study of the two polymorphs has been carried out on Beagle female dogs, treated them by oral route with a dose of 100 mg/kg in capsule of one of the polymorphs, collecting blood samples from the jugular vein of each animal before each dosing and 1, 2, 4, 6, 8 and 24 hours after each dosing, transferring the samples into tubes containing heparin and separating the plasma by centrifugation.

The plasma has been assayed for rifaximin on the validated LC-MS/MS method and the maximum observed plasma concentration (Cmax), the time to reach the Cmax (Tmax), and the area under the concentration-time curve (AUC) have been calculated.

The experimental data reported in the following table 1 clearly show that rifaximin ε is negligibly absorbed, while rifaximin δ is absorbed at a value (Cmax=0.308 µg/ml) comprised in the range of from 0.1 to 1.0 µg/ml.

TABLE 1

Pharmacokinetic parameters for rifaximin polymorphs following
single oral administration of 100 mg/kg by capsules to female dogs

|  | Cmax ng/ml Mean | Tmax h Mean | AUC0-24 ng · h/ml Mean |
|---|---|---|---|
| Polymorph δ | 308.31 | 2 | 801 |
| Polymorph ε | 6.86 | 4 | 42 |

The above experimental results further point out the differences existing among the two rifaximin polymorphs.

The forms δ and ε can be advantageously used in the production of medicinal preparations having antibiotic activity, containing rifaximin, for both oral and topical use. The medicinal preparations for oral use contain the rifaximin δ and ε together with the usual excipients as diluting agents like mannitol, lactose and sorbitol; binding agents like starches, gelatins, sugars, cellulose derivatives, natural gums and polyvinylpyrrolidone; lubricating agents like talc, stearates, hydrogenated vegetable oils, polyethylenglycol and colloidal silicon dioxide: disintegrating agents like starches, celluloses, alginates, gums and reticulated polymers; coloring, flavoring and sweetening agents.

All the solid preparations administrable by oral route can be used in the ambit of the present invention, for instance coated and uncoated tablets, capsules made of soft and hard gelatin, sugar-coated pills, lozenges, wafer sheets, pellets and powders in sealed packets.

The medicinal preparations for topical use contain the rifaximin δ and ε together with the usual excipients like white petrolatum, white wax, lanoline and derivatives thereof, stearylic alcohol, propylenglycol, sodium lauryl sulfate, ethers of the fatty polyoxyethylene alcohols, esters of the fatty polyoxyethylene acids, sorbitan monostearate, glyceryl monostearate, propylene glycol monostearate, polyethylene glycols, methylcellulose, hydroxymethylpropylcellulose, sodium carboxymethylcellulose, colloidal aluminum and magnesium silicate, sodium alginate.

All the topical preparations can be used in the ambit of the present invention, for instance the ointments, the pomades, the creams, the gels and the lotions.

The invention is herein below illustrated from some examples that do not have to be taken as a limitation of the invention: from what described results in fact evident that the forms δ and ε can be obtained by suitably combining between them the above mentioned conditions of crystallization and drying.

Example 1

Preparation of Raw Rifaximin and of Dried Raw Rifaximin

In a three-necked flask equipped with mechanic stirrer, thermometer and reflux condenser, 120 ml of demineralized water, 96 ml of ethyl alcohol, 63.5 g of rifamycin O and 27.2 g of 2-amino-4-methylpyridine are loaded in succession at room temperature. After the loading, the mass is heated at 47±3° C., is kept under stirring at this temperature for 5 hours, then is cooled to 20±3° C. and, during 30 minutes, is added with a mixture, prepared separately, made of 9 ml of demineralized water, 12.6 ml of ethyl alcohol, 1.68 g of ascorbic acid and 9.28 g of aqueous concentrated hydrochloric acid. At the end of the addition, the mass is kept under stirring for 30 minutes at an interior temperature of 20±3° C. and then, at the same temperature, 7.72 g of concentrated hydrochloric acid are dripped until a pH equal to 2.0.

At the end of the addition, the mass is kept under stirring, always at an interior temperature equal to 20° C., for 30 minutes, then the precipitate is filtered and washed by means of a mixture made of 32 ml of demineralized water and of 25 ml of ethyl alcohol. The so obtained "raw rifaximin" (89.2 g) is dried under vacuum at room temperature for 12 hours obtaining 64.4 g of "dried raw rifaximin" which shows a water content equal to 5.6%. The product by further drying under vacuum until the weight of 62.2 g of dried raw rifaximin having a water content equal to 3.3%, whose diffractogram corresponds to the polymorphous form δ characterized from a powder X-ray diffractogram showing peaks at values of angles 2θ of 5.7°35 0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2, 21.5°±0.2. The product is hygroscopic.

Example 2

Preparation of Rifaximin ε

Example 1 is repeated and after having obtained the δ form, the solid powder is further dried under vacuum for 24 hours at the temperature of 65° C. The product obtained is rifaximin s characterized from a powder X-ray diffractogram showing peaks at values of angles 2θ of 7.0°±0.2, 7.3°±0.2, 8.2°±0.2, 8.7°±0.2, 10.3°±0.2, 11.1°±0.2, 11.7°±0.2, 12.4°±0.2, 14.5°±0.2, 16.3°±0.2, 17.2°±0.2, 18.0°±0.2, 19.4°±0.2.

Example 3

Bioavailability in Dogs By Oral Route

Eight pure-bred Beagle females dogs having 20 weeks of age and weighing between 5.0 and 7.5 kg have been divided into two groups of four.

The first of these group has been treated with rifaximin δ, the second with rifaximin ε according to the following procedure.

To each dog have been administered by the oral route 100 mg/kg of one of the rifaximin polymorphs into gelatin capsules and blood samples of 2 ml each have been collected from the jugular vein of each animal before each dispensing and 1, 2, 4, 6, 8 and 24 hours after the administration.

Each sample has been transferred into a tube containing heparin as anticoagulant and has been centrifuged; the plasma has been divided into two aliquots, each of 500 μl, and has been frozen at −20° C.

The rifaximin contained in the plasma has been assayed by means of the validated LC-MS/MS method and the following parameters have been calculated according to standard non-compartmental analysis:

Cmax=maximum observed plasma concentration of rifaximin in the plasma;

Tmax=time at which the Cmax is reached;

AUC=area under the concentration-time curve calculated through the linear trapezoidal rule.

The results reported in the table 1 clearly show how the rifaximin δ is much more absorbed, more than 40 times, in respect of rifaximin ε, which is practically not absorbed.

What is claimed is:

1. A method of treating bacterial activity in the gastrointestinal tract of a subject, the method comprising:

orally administering to the subject a pharmaceutical composition comprising a therapeutically effective amount of rifaximin δ together with a pharmaceutically acceptable excipient selected from the group consisting of diluting, binding, lubricating, disintegrating, colouring, flavouring and sweetening agents, wherein rifaximin δ has a powder X-ray diffractogram showing peaks at values of the diffraction angles 2θ of about 5.7°±0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2, 21.5°±0.2.

2. The method of claim 1, wherein the pharmaceutical composition is in a formulation selected from the group consisting of coated or uncoated tablet, hard or soft gelatin capsule, sugar-coated pill, lozenge, wafer sheet, pellet, and powder in sealed packet.

3. A method of treating bacterial activity in the gastrointestinal tract of a subject, the method comprising:

topically administering to the subject a pharmaceutical composition comprising a therapeutically effective amount of rifaximin δ, wherein rifaximin δ has a powder X-ray diffractogram showing peaks at values of the diffraction angles 2θ of about 5.7°±0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2, 21.5°±0.2.

4. The method of claim 3, wherein the pharmaceutical composition is in a formulation selected from the group consisting of ointment, pomade, cream, gel and lotion.

5. The method of claim 1, wherein rifaximin δ has a water content between 3.0% and 4.5%.

6. A method of treating bacterial activity in the gastrointestinal tract of a subject, the method comprising:

orally administering to the subject by oral route a pharmaceutical composition comprising a therapeutically effective amount of rifaximin ε together with a pharmaceutically acceptable excipient selected from the group consisting of diluting, binding, lubricating, disintegrating, colouring, flavouring and sweetening agents, wherein rifaximin ε has a powder X-ray diffractogram showing peaks at values of the diffraction angles 2θ of 7.0°±0.2, 7.3°±0.2, 8.2°±0.2, 8.7°±0.2, 10.3°±0.2, 11.1°±0.2, 11.7°±0.2, 12.4°±0.2, 14.5°±0.2, 16.3°±0.2, 17.2°±0.2, 18.0°±0.2, 19.4°±0.2.

7. The method of claim 6, wherein the pharmaceutical composition is in a formulation selected from the group consisting of coated or uncoated tablet, hard or soft gelatin capsule, sugar-coated pill, lozenge, wafer sheet, pellet, and powder in sealed packet.

8. A method of treating bacterial activity in the gastrointestinal tract of a subject, the method comprising:

topically administering to the subject by oral route a pharmaceutical composition comprising a therapeutically effective amount of rifaximin ε, wherein rifaximin ε has a powder X-ray diffractogram showing peaks at values of the diffraction angles 2θ of 7.0°±0.2, 7.3°±0.2, 8.2°±0.2, 8.7°±0.2, 10.3°±0.2, 11.1°±0.2, 11.7°±0.2, 12.4°±0.2, 14.5°±0.2, 16.3°±0.2, 17.2°±0.2, 18.0°±0.2, 19.4°±0.2.

9. The method of claim 8, wherein the pharmaceutical composition is in a formulation selected from the group consisting of ointment, pomade, cream, gel and lotion.

* * * * *